United States Patent [19]

Beard

[11] 4,191,764
[45] Mar. 4, 1980

[54] 5(6)-BENZENE RING SUBSTITUTED BENZIMIDAZOLE-2-CARBAMATE DERIVATIVES HAVING ANTHELMINTIC ACTIVITY

[75] Inventor: Colin C. Beard, Palo Alto, Calif.

[73] Assignee: Syntex (U.S.A.) Inc., Palo Alto, Calif.

[21] Appl. No.: 946,985

[22] Filed: Sep. 29, 1978

Related U.S. Application Data

[60] Division of Ser. No. 758,112, Jan. 10, 1977, Pat. No. 4,139,626, which is a continuation-in-part of Ser. No. 668,778, Mar. 19, 1976, abandoned.

[51] Int. Cl.² .................. A61K 31/535; C07D 295/18
[52] U.S. Cl. ............................... 424/248.55; 544/139
[58] Field of Search ............... 544/139; 424/248.55

[56] References Cited

PUBLICATIONS

Luk'yanova et al., "Chem. Abstracts", vol. 86, No. 73805b (1977).

*Primary Examiner*—Alan L. Rotman
*Assistant Examiner*—R. W. Ramsuer
*Attorney, Agent, or Firm*—Tom M. Moran; Joseph I. Hirsch

[57] ABSTRACT

Benzene ring substituted benzimidazole-2-carbamate derivatives represented by the formula:

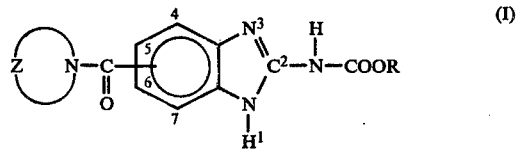

where R is a lower alkyl group having 1 to 4 carbon atoms;

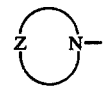

is a 5, 6, 7 or 8 membered heterocyclic ring containing 1 or 2 hetero atoms; the

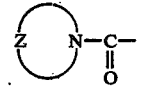

substitution being at the 5(6)-position; and the pharmaceutically acceptable salts thereof. The compounds are useful as pesticides, particularly as anthelmintic and antifungal agents.

16 Claims, No Drawings

5(6)-BENZENE RING SUBSTITUTED BENZIMIDAZOLE-2-CARBAMATE DERIVATIVES HAVING ANTHELMINTIC ACTIVITY

REFERENCE TO PARENT APPLICATION

This is a division of U.S. application Ser. No. 758,112 filed Jan. 10, 1977, now U.S. Pat. No. 4,139,626 which in turn is a continuation-in-part of U.S. Patent Application Ser. No. 668,778 filed Mar. 19, 1976 abandoned.

FIELD OF THE INVENTION

This invention relates to novel chemical compounds. More particularly, this invention relates to novel anthelmintically active benzimidazole-2-carbamate derivatives wherein the benzene ring is substituted at the 5(6)-position.

BACKGROUND OF THE INVENTION

1-Position isomers of certain of the 5(6)-substituted benzimidazole-2-carbamates described and claimed herein are suggested in this art (for example, see U.S. Letters Pat. Nos. 3,541,213 and 3,626,070). Related antifungal compounds are also shown in French Pat. No. 2,054,799.

SUMMARY OF THE INVENTION

The novel benzene ring substituted benzimidazole-2-carbamate derivatives of the present invention can be represented by the following formula:

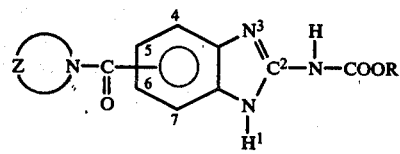

where R is a lower alkyl group having 1 to 4 carbon atoms;

is a 5, 6, 7 or 8 membered heterocyclic ring containing 1 or 2 hetero atoms; the

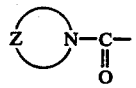

substitution being at the 5(6)-position; and the pharmaceutically acceptable salts thereof. These benzimidazole-2-carbomate derivatives are useful as anthelmintics and antifungals and may be formulated with suitable pharmaceutical or industrial carriers. These compounds are very useful as aqueous, injectable solutions.

DETAILED DESCRIPTION OF THE INVENTION

Compounds of the Invention

In the above definition of the invention, the term "heterocyclic ring" refers to both substituted and unsubstituted heterocyclic rings having 5, 6, 7 or 8 total ring atoms and containing 1 or 2 hetero atoms, and includes both saturated and mono- or di-olefinically unsaturated heterocyclic rings. The heterocyclic ring can be substituted with one hydroxy, phenyl, benzyl or oxo radical, or one or two alkyl groups. The second hetero atom, if the ring contains two hetero atoms, can be nitrogen, oxygen or sulfur, with the sulfur being in the sulfide, sulfoxide or sulfone form and the additional nitrogen atom, if present in the ring, being substituted with phenyl, benzyl or an alkyl group. Typical heterocyclic rings, expressed in radical form, include, for example, pyrrolidinyl; piperidino; 4-hydroxypiperidino; 2-methylpiperidino; 3-methylpiperidino; 4-methylpiperidino; 2,6-dimethylpiperidino; 4-phenylpiperidino; 4-benzylpiperidino; piperazinyl; 4-alkylpiperazinyl (such as 4-methylpiperazinyl); 4-phenylpiperazinyl; 4-benzylpiperazinyl; morpholino; 2,6-dimethylmorpholino; 4-oxo-1,4-dihydropyridyl; 1,2,3,6-tetrahydropyridyl; thiazolidin-3-yl; 1-oxo-thiazolidin-3-yl; 1,1-dioxo-thiazolidin-3-yl; thiomorpholino; 1-oxo-thiomorpholino; 1,1-dioxo-thiomorpholino; pyrrolinyl; perhydroazepinyl; perhydroazocinyl; imidazolinyl; oxazolidinyl; tetrahydroazinyl; tetrahydrothiazinyl; and the like.

A subgroup of the heterocyclic rings of the present invention, expressed in radical form, includes the following heterocyclic rings: 4-hydroxypiperidino; 2-methylpiperidino; 3-methylpiperidino; 4-methylpiperidino; 2,6-dimethylpiperidino; 4-phenylpiperidino; 4-benzylpiperidino; piperazinyl; 4-methylpiperazinyl; 4-phenylpiperazinyl; 4-benzylpiperazinyl; 2,6-dimethylmorpholino; 1,2,3,6-tetrahydropyridyl; 4-oxo-1,4-dihydropyridyl; thiazolidin-3-yl; 1-oxo-thiazolidin-3-yl; morpholino; thiomorpholino; 1-oxo-thiomorpholino; and pyrrolinyl.

A further subgroup of the heterocyclic rings of the present invention includes the following heterocyclic rings, also expressed in radical form: 4-hydroxypiperidino; 4-phenylpiperidino; 4-benzylpiperidino; piperazinyl; 4-methylpiperazinyl; 4-phenylpiperazinyl; 4-benzylpiperazinyl; 1,2,3,6-tetrahydropyridyl; 4-oxo-1,4-dihydropyridyl; thiazolidin-3-yl; 1-oxo-thiazolidin-3-yl; morpholino; 1-oxo-thiomorpholino; and pyrrolinyl.

The hydrogen on the nitrogen at the 1-position of the benzimidazole ring can be replaced with one of the following substituents: N-alkylcarbamoyl (for example, methylcarbamoyl or n-butylcarbamoyl), N,N-dialkylcarbamoyl, N-alkoxycarbonylcarbamoyl, phenylcarbamoyl, cyano, trichloromethylthio, alkylthio, phenylthio, nitrophenylthio, alkylsulfinyl, phenylsulfinyl, alkanoyl, alkoxycarbonyl, alkoxycarbonylalkylcarbonyl, alkyl, alkenyl, benzyl, benzoyl, alkoxyalkyl, alkoxycarbonylalkyl, carboxyalkyl, hydroxy and conventional esters and ethers thereof, etc. These compounds can be prepared from the compounds of Formula I by the appropriate substitution reaction with isocyanates as described in South African Pat. No. 74/6665.

As used in this specification and claims, the term "lower alkyl" refers to both straight and branched chain alkyl groups having from 1 through 4 carbon atoms and thus includes primary, secondary and tertiary alkyl groups. Typical lower alkyls include, for example, methyl, ethyl, n-propyl, isopropyl, n-butyl, isobutyl, and t-butyl. The term "alkyl" refers to both straight and branched chain alkyl groups having 1 to 6 carbon atoms and thus includes those listed above with respect to "lower alkyl" and, for example, n-pentyl, isopentyl, n-hexyl, and the like. The term "alkenyl" refers to an unsaturated hydrocarbon group having from 3 to 6 carbon atoms and a single carbon-carbon double bond, provided that the double bond cannot be on the α-carbon atom. Typical alkenyl groups include, for example, 2-propenyl, 2-butenyl, 3-butenyl, and the like. The term "alkoxy" refers to the group having the formula $R^3O$— wherein $R^3$ is an alkyl group as defined above. Typical alkoxy groups include, for example, methoxy, ethoxy, t-butoxy, hexyloxy, and the like. The terms "alkylthio" and "alkylsulfinyl" refer to those groups having the formula $R^3S$— and

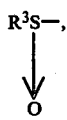

respectively, where $R^3$ is an alkyl group as defined above. The term "alkanoyl" refers to alkanoyl groups derived from carboxylic acids having 1 through 6 carbon atoms such as acetyl, propionyl, butyryl, valeryl, isovaleryl, hexanoyl and the like.

Exemplary of the compounds of the present invention, as represented by Formula I above, are the following illustrative compounds:

5(6)-(pyrrolidinylcarbonyl)-2-carbomethoxyaminobenzimidazole;

5(6)-piperidinocarbonyl-2-carbomethoxyaminobenzimidazole;

5(6)-(4-hydroxypiperidinocarbonyl)-2-carbomethoxyaminobenzimidazole;

5(6)-(2,6-dimethylpiperidinocarbonyl)-2-carbomethoxyaminobenzimidazole;

5(6)-(1,2,3,6-tetrahydropyridylcarbonyl)-2-carbomethoxyaminobenzimidazole;

5(6)-(4-methylpiperazinylcarbonyl)-2-carbomethoxyaminobenzimidazole;

5(6)-morpholinocarbonyl-2-carbomethoxyaminobenzimidazole;

5(6)-(2,6-dimethylmorpholinocarbonyl)-2-carbomethoxyaminobenzimidazole;

5(6)-thiomorpholinocarbonyl-2-carbomethoxyaminobenzimidazole;

5(6)-(1-oxo-thiomorpholinocarbonyl)-2-carbomethoxyaminobenzimidazole;

5(6)-(thiazolidin-3-yl)-2-carbomethoxyaminobenzimidazole;

5(6)-(1-oxo-thiazolidin-3-yl)-2-carbomethoxyaminobenzimidazole;

5(6)-(2-methylpiperidinocarbonyl)-2-carbomethoxyaminobenzimidazole;

5(6)-(3-methylpiperidinocarbonyl)-2-carbomethoxyaminobenzimidazole;

5(6)-(4-methylpiperidinocarbonyl)-2-carbomethoxyaminobenzimidazole; and the corresponding 2-carbethoxyamino-2-carbopropoxyamino-, or 2-carbobutoxyamino-compounds.

Of the above compounds, 5(6)-morpholinocarbonyl-2-carbomethoxyaminobenzimidazole is presently preferred because of the substantial activity thereof against the helminths specifically referred to above.

Where the compound has a basic moiety, the term "pharmaceutically acceptable salts" refers to those salts prepared from non-toxic inorganic or organic acids, such as those salts conventionally used in the art. Such salts include, for example, salts of inorganic acids such as, for example, sulfuric, sulfonic, sulfamic, nitric, phosphoric, hydrochloric acids and the like, and salts of organic acids such as, for example, acetic, citric, lactic, palmitic, tartaric, succinic, maleic, benzoic acids and the like.

UTILITY AND ADMINISTRATION

The compounds of the present invention, and the pharmaceutically acceptable salts thereof, possess broad spectrum activity against parasites of mammals (human or animal), including both mature and immature parasitic forms, as represented for example, by the genera Trichostronglylus, Haemonchus, Ostertagia, Cooperia, Nematodirus, and Stronglyoides, and specifically, for example against *Nematospiroides dubius, Hymenolepis Nana, Syphacia obvelata,* and/or *Aspiculuris tetraptera.* In particular, these compounds are found to exhibit high activity against various helminthic infections of the intestinal tract of economically important animals, coupled with low systemic toxicity to the host animal.

The compounds of the present invention are also useful as antifungal agents, particularly as systemic fungicides for controlling fungal diseases of plants of economic importance.

The amount of the compound to be administered will depend upon the actual compound utilized, and upon the weight of the animal being treated. In general, however, the daily dosage level will usually be between about 0.5 mg/kg and 100 mg/kg of body weight of the animal being treated. The active ingredient is adapted to be administered to the animal by mixing it with the diet of the animal, as with a feed mix, or formulating it with a non-toxic carrier to give anthelmintic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, agar, pectin or the like. Examples of suitable liquid carriers are peanut oil, sesame oil and water.

A wide variety of pharmaceutical forms can be employed in those cases wherein the medicament is not admixed with the feed. Thus, if a solid carrier is used, the compound can be administered in tablet or capsule form. If a liquid carrier is used, the medicament may be in the form of a soft gelatin capsule, a liquid suspension, or a solution suitable for injection. Because the salts of the compounds of this invention are very water soluble, aqueous solutions or suspensions are preferred.

PROCESS FOR PREPARATION

In general, the compounds of the present invention can be prepared by six basic routes. (A) In the first route, the 4-heterocyclic carbonyl-1,2-phenylenediamine compound is reacted with a suitable reactant to form the products of this invention directly. (B) In a second process the 4-heterocyclic carbonyl-1,2-phenylenediamine is reacted with a suitable reactant to form an intermediate thioureido compound which is then cyclized to form the compounds of the invention represented by formula I. (C) A third process of preparing the compounds of this invention comprises reacting the 4-heterocyclic carbonyl-1,2-phenylenediamine with a suitable reagent to form a 2-amino-5(6)-heterocyclic carbonylbenzimidazole and reacting that intermediate with a carboxylating agent to give the products of this invention. (D) In a fourth process, 3,4-diaminobenzoic acid is reacted with a suitable reagent to form the benzimidazole carbamate substituted at the 5(6) position with a carboxylic acid, then reacting that compound with a heterocyclic compound to form the desired product of this invention represented by formula I. (E) In a fifth process 2-nitro-4-heterocyclic carbonyl-aniline is converted to the corresponding 2-nitro-4-heterocyclic carbonyl-carbalkoxythioureidobenzene which is then reduced to the corresponding 2-amino compound which in turn is cyclized to form a compound of this invention. The cyclization may either be a one step procedure or a two step procedure wherein an intermediate dithioureido compound is first formed which in turn is cyclized. (F) In the sixth process 1-acylamino-2-nitro-4-heterocycliccarbonylbenzene is reduced to form 1-acylamino-2-amino-4-heterocycliccarbonylbenzene which is then reacted to form 1-acylamino-2-carbalkoxythioureido-4-heterocycliccarbonylbenzene which may then be treated with acid or base to form the corresponding 1-amino-2-carboalkoxythioureido compound, which in turn is cyclized to form a compound of this invention or may be reacted to form the bis-carbalkoxythioureido compound.

Once the desired compound of this invention is obtained, if it has a sulfur atom in the heterocyclic ring, the sulfur atom may be converted to a sulfoxide and the sulfoxide to a sulfone by treating with a suitable oxidizing agent such as a peracid, e.g., peracetic acid, in a suitable solvent at temperatures of about −30° C. to 25° C. as discussed hereafter.

It will be appreciated that the compounds of this invention exist as a free base or as a salt. The free base is readily converted to a salt by reacting equimolar portions of the free base and a suitable organic or inorganic acid, as discussed hereinbefore. Conversely, the salt is converted into the free base by treating the salt with at least a molar equivalent of an appropriate organic or inorganic base.

The intermediate mono- and bis-carbalkoxythioureido compounds are also useful as anthelmintics since these compounds show anthelmintic activity.

The starting materials for these six basic processes can be prepared by methods discussed hereafter.

An overall reaction scheme setting forth the process for making the compounds of this invention is set forth as follows:

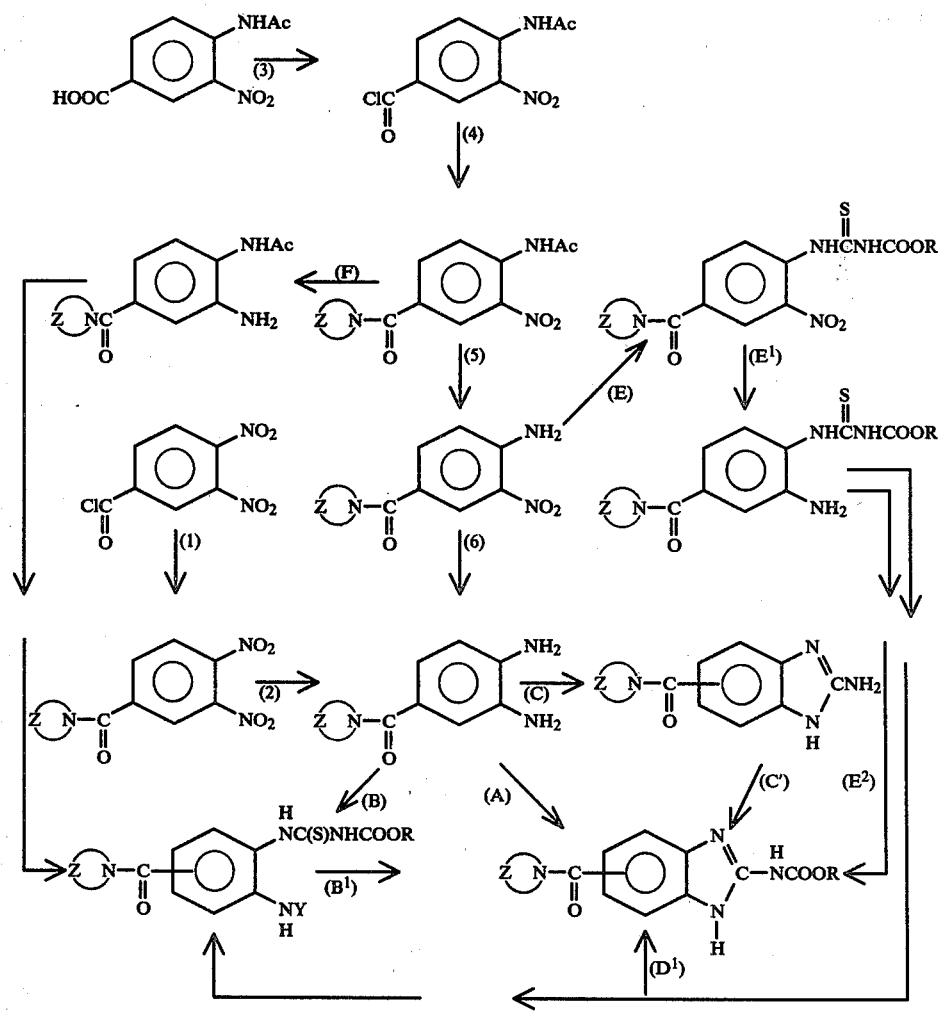

-continued

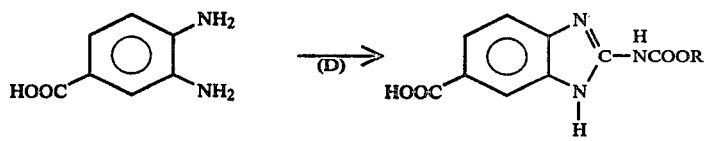

(A) The first process for making the compounds of this invention is set forth in the following reaction scheme.

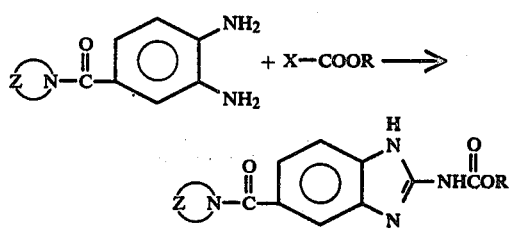

wherein R and

have the value set forth hereinbefore, X is chosen from the group consisting of

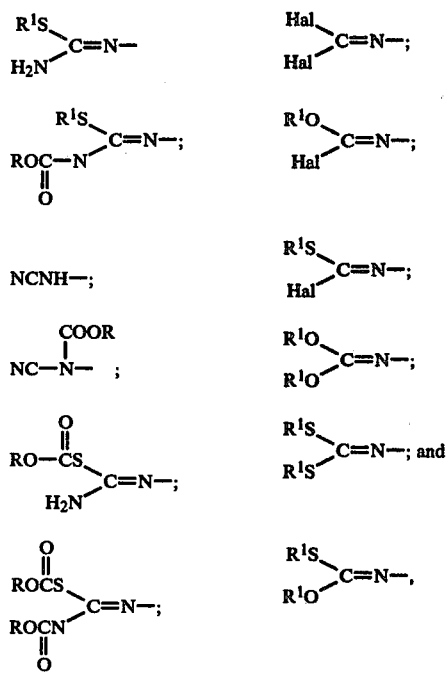

wherein Hal is chloro, bromo or iodo, and $R^1$ is lower alkyl, aralkyl of 7 or 8 carbon atoms (especially benzyl) or alkylene sulfonic acid of 2-4 carbons or the alkali metal salt thereof such as propylene sulfonic acid and the salts such as sodium, potassium and the like.

In general, the diamino compounds are converted to the corresponding benzimidazole 2-carbamate compounds by reacting the diamino group with the XCOOR reagent in a suitable protic solvent such as water or an alcohol such as methanol or ethanol at temperatures of about 20° to 100° C., preferably under reflux conditions for about from ½ to six hours.

Preferably, the diamino compounds are converted to the corresponding benzimidazole 2-carbamate compounds directly, as exemplified by steps (A) and (C) above, by reacting the diamino compound with (i) a reagent believed to be a 1-mono- or 1,3-bis(alkoxycarbonyl)-S-alkyl isothiourea, for example 1,3-bis(methoxycarbonyl)-S-methyl isothiourea or 1,3-bis(ethoxycarbonyl)-S-methyl isothiourea, or (ii) a mono- or bis(alkoxycarbonyl)cyanamide, e.g., bis (methoxycarbonyl) cyanamide, in an aqueous alcoholic medium, for example, aq. methanol or aq. ethanol, at from about room temperature to the reflux temperature of the reaction medium for about ½ to about 6 hours. The reaction medium is preferably made acidic to a pH of about 4-6 with, for example, a sufficient amount (e.g., 1-2 moles) of acetic acid. About 1-2 moles, generally about 1.1 moles, of the XCOOR reagent are utilized per mole of the diamino compound.

The preferred reagent believed to be the 1-mono- or 1,3-bis(alkoxycarbonyl)-S-alkyl isothiourea is prepared by reacting thiourea with about equimolar amounts alkyl sulfate or alkylchloroformate at elevated temperatures, e.g. about 20° to 100° C. to form S-alkyl isothiourea (or the $H_2SO_4$ or HCl salt thereof) which is then reacted with a molar excess of alkyl chloroformate (more than 1 mole of the alkylchloroformate per mole of the S-alkyl isothiourea and preferably about 1.9-2.5 moles of the former per mole of the latter) in the presence of a suitable aqueous base, such as sodium hydroxide, potassium hydroxide and the like, at low temperatures of about 0° to 50° C. for about 3 hours. The resulting reagent is substantially insoluble in water and so may be filtered off and used in the process of this invention. Alternatively the desired reagent (II) may be extracted with a suitable organic solvent such as a chlorinated hydrocarbon such as methylene chloride and the like, benzene, toluene, or other hydrocarbon solvents and isolated by evaporating the solvent. The reagent is preferably utilized in situ to carry out the process of this invention.

(B) The second process for making the compounds of this invention may be represented by the following reaction scheme:

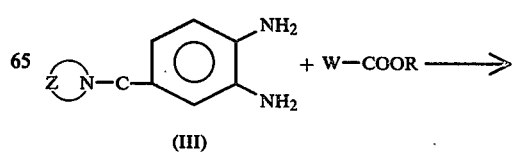

-continued

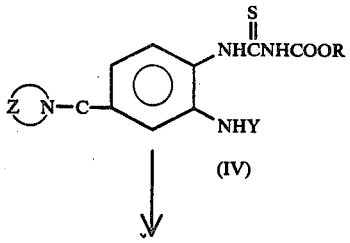

(IV)

↓

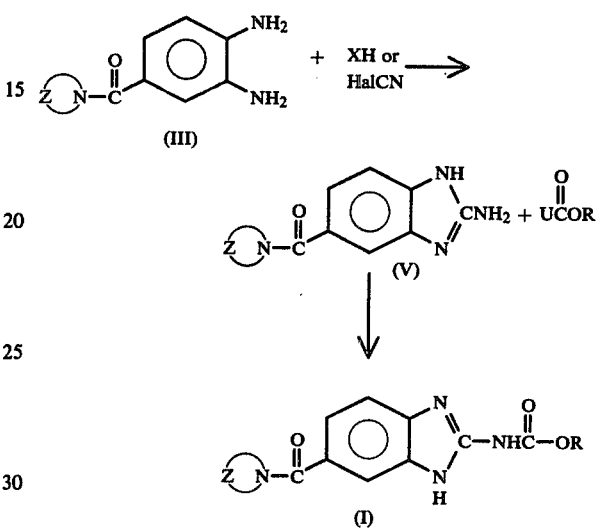

wherein Y is hydrogen, COR, COOR or CSNHCOOR and W is —NCS, i.e. WCOOR is an alkoxycarbonyl isothiocyanate. In this reaction scheme, the diamine is reacted with a suitable reagent to form the corresponding thioureido compound indicated as formula IV wherein Y is preferably H or C(S)NHCOOR. In this step the diamine and the reagent are reacted in a suitable inert solvent such as acetone, tetrahydrofuran, dioxane, or dimethylformamide at temperature of about 0° C. to 100° C. until the thioureido compound is obtained.

Preferably, the conversion of the diamino compound prepared in step (2) or (6) to the corresponding bis(carbalkoxythioureido)-compound, as exemplified by step (B) above, is achieved by reacting the diamino compound with an alkoxy carbonyl isothiocyanate, such as methoxy carbonyl isothiocyanate or ethoxy carbonyl isothiocyanate, in an inert reaction medium, such as acetone, tetrahydrofuran, dioxane, or dimethylformamide. This reaction is typically conducted at a temperature from about 0° C. to about 60° C., generally about room temperature, for about ¼ hour to about 120 hours using an excess of the isothiocyanate reactant, generally about a two-fold molar excess.

Cyclization of the bis(carbalkoxythioureido) compound may be conducted in the presence of a suitable metal ion catalyst such as Cu++, Hg++, Pb++ and the like, preferably cupric acetate in a mixture of acetic acid and water. This treatment, which may also be conducted on the mono(carbalkoxythioureido)-monoamino compound, is generally conducted at about 40° C. to about 120° C. for about ½ to 24 hours. Alternatively, the carbalkoxythioureido compound may first be alkylated with an alkyl halide or a dialkyl sulfate, e.g., methyl chloride or dimethyl sulfate, to form the S alkyl carbalkoxythioureido compound which is then cyclized by heating to about 60° to 120° C., preferably about 70° C., at a pH of about 3-7. In still another alternative cyclization, the carbalkoxythioureido compound is oxidized using a peracid such as peracetic acid to form a compound represented by the formula

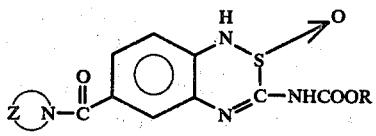

which in turn is heated to about 60° to 100° C. under acidic conditions to give a compound of this invention. See German Offenlegungschrift No. 2,246,605 to I.C.I.

(C) In a third process for making the compounds of this invention, the 4-heterocyclic carbonyl-1,2-phenylenediamine is converted to the 2-amino-5(6)-heterocyclic carbonyl benzimidazole which in turn is converted to the compound of this invention according to the following reaction scheme wherein X and Hal are defined as set forth above and U is chloro, alkoxy of 1-6 carbon atoms (RO—) or alkylthio of 1-6 carbon atoms (RS—).

In the formation of the 2-amino-benzimidazole, the XH or HalCN compound is reacted with the diamine in a suitable solvent such as toluene, methylene chloride, methanol, ethanol, tetrahydrofuran, water at temperatures of about 0° to 100° C. for about one to ten hours. The resulting 2-aminobenzimidazole is reacted at temperatures of about −20° to 100° C. with a suitable haloformate ester, a carbonate or a thiocarbonate in a suitable organic or inorganic solvent such as toluene, methylene chloride, alcohols (e.g. methanol, ethanol, isopropanol), tetrahydrofuran, pyridine, and the like alone or, preferably, in the presence of an organic or inorganic base such as tertiary amines (trimethylamine, triethylamine, etc.) pyridine, morpholine, alkali metal alkoxides such as sodium methoxide, and the like, carbonate, alkali metal hydroxide such as sodium hydroxide, and the like.

(D) In a fourth process for making compounds of this invention, the 5(6)-carboxy-2-alkoxycarbonylaminobenzimidazole is converted to the compounds of this invention by converting the carboxy to the heterocyclic carbonyl

First the carboxy group is converted into an acid chloride or mixed anhydride which in turn is reacted with the appropriate heterocyclic compound. Generally, one equivalent of the heterocyclic base

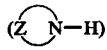

and an additional equivalent of an organic base (which may be the heterocyclic base or triethylamine) is reacted with the acid chloride or anhydride in an inert solvent such as, for example, tetrahydrofuran, benzene or methylene chloride, at about 0° C. to about 80° C. for about ¼ to about 24 hours to yield the desired compound of this invention. The acid chloride or mixed anhydride is readily prepared by conventional methods well known in the art for example from the corresponding acid and thionyl chloride or from trifluoroacetic anhydride, respectively.

(E) A fifth alternative method of making the compounds of this invention is set forth in the following reaction scheme in turn is cyclized according to the procedure set forth in Part (B) to give the product of this invention.

Alternatively the monothiouredio compound (VI) may be further reacted with an alkoxycarbonyl isothiocyanate to form the bis thioureido compound which is then cyclized acording to the procedure of step (B).

(F) The sixth alternative process may be represented by the following reaction scheme:

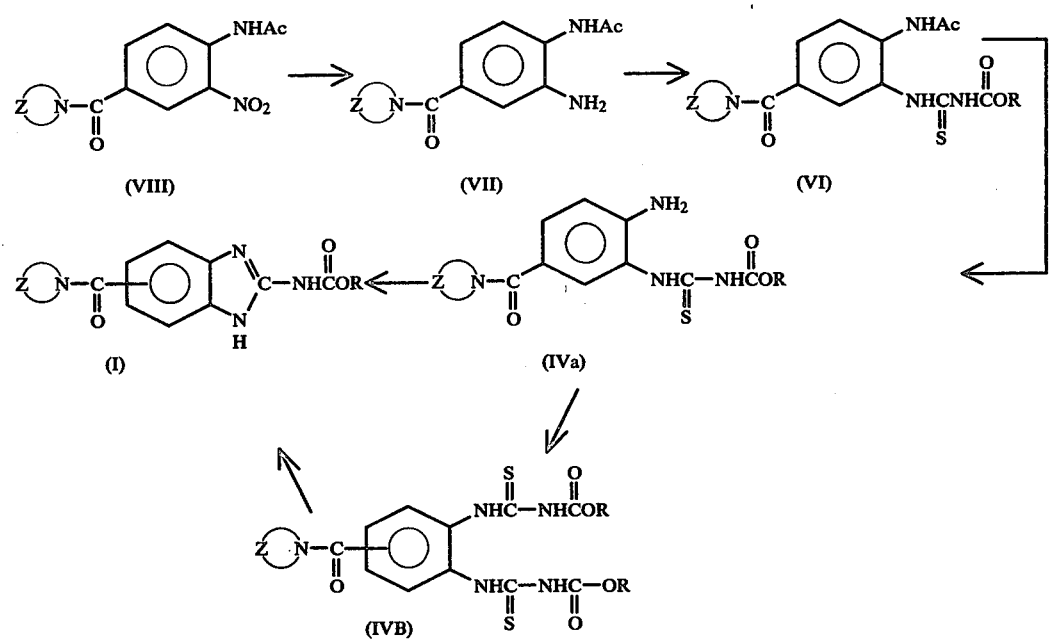

Thus in this process the nitrobenzene compound, represented by formula VIII, is reduced to form the aminobenzene compound, represented by formula VII. This reduction may be performed using any of the processes discussed hereinbefore or hereafter. The resulting aminobenzene compound is converted to the corresponding carbalkoxy thioureido compound VI by reacting the aminobenzene compound VII with a suitable reagent such as that used in step A for the first process for making the compounds of this invention, hereinbefore described. Once the carbalkoxy thioureido compound VI is obtained, it is treated with a suitable strong acid or base under conditions suitable to hydrolyze the acyl (Ac in the formulae) and form the monocarbalkoxythioureido compound indicated as IVa. This product in turn can be cyclized by heating as discussed in the discussion of step B for making the compounds of this

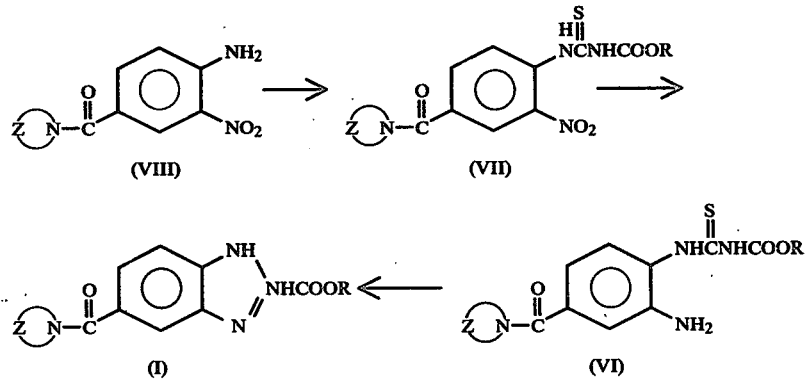

In this case the 2-nitro-4-heterocyclic carbonyl aniline compound is reacted with a reagent such as one set forth in process (B) to give the 2-nitro-4-heterocyclic carbonyl phenyl thioureido compound. Thereafter, the nitro group of that compound is then reduced using a suitable reducing agent such as ferric sulfate in methanol to form the corresponding amino compound which invention or may be further reacted with a reagent to form the bis thioureido compound indicated as IVb which in turn may be cyclized to form the compound of this invention. Both the mono and bis carbalkoxy thioureido compounds show anthelmintic activity and thus are useful as anthelmintics themselves. The intermediate monocarboalkoxy isothioureido compound is the position isomer of the monocarbalkoxyisothioureido compound formed as discussed in part E, i.e. the fifth process for making the products of this invention.

PREPARATION OF STARTING MATERIALS

The reaction of 3,4-dinitrobenzoyl chloride, or 4-acetamido-3-nitrobenzoylchloride with the appropriate heterocyclic compound, as exemplified by steps (1) and (4) above, respectively, can be effected by reacting the benzoylchloride starting material with two equivalents of the heterocyclic base

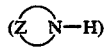

or one equivalent of the heterocyclic base plus one equivalent of triethylamine in an inert solvent, such as, for example, tetrahydrofuran, benzene or methylene chloride, at about 0° C. to about 80° C. for about ¼ to about 24 hours. In a similar manner, the 5(6)-carboxy-2-carbalkoxyaminobenzimidazole can be reacted, as exemplified by step (D¹) above, with the heterocyclic base to afford the desired compound of Formula I. In this later procedure, the 5(6)-carboxy-2-carbalkoxyaminobenzimidazole is first converted to an activated intermediate thereof, as by treatment with trifluoroacetic acid, an alkyl chloroformate or thionyl chloride, and then reacted with the heterocyclic base as set forth above.

Reduction of a nitro group to amino group, as exemplified by steps (2), (6) and (E') above, can be effected by a variety of techniques, for example, the nitro group can be catalytically reduced utilizing hydrogen over a palladium/charcoal catalyst. This reaction is conducted in an inert solvent, such as methanol, at a temperature from about 0° C. to 35° C., generally about room temperature, for about ½ to about 2 hours. Other suitable inert solvents include ethyl acetate, acetic acid, and ethanol.

Another suitable reducing technique is to treat the nitro group-containing compound with stannous chloride in concentrated hydrochloric acid at a temperature in a range from about −20° C. to about 100° C., generally about room temperature, for about ½ to about 6 hours. An excess of the stannous chloride reactant should be utilized, generally about 5 parts (by weight) per unit weight of the starting compound.

The reduction can also be conducted using sodium dithionite (sodium hydrosulfite) in basic aqueous methanol at other alkanols such as ethanol or propanol) with hydrazine in the presence of a "boride" catalyst [for example, generated from ferrous sulfate, cobalt chloride or nickel sulfate and sodium borohydride] at lower temperatures such as about 20° C. to the reflux temperature for about ½ to 24 hours; or by treating the nitro-containing compound with iron powder and a ferrous salt, such as ferrous sulfate or ferrous chloride, in aqueous methanol at reflux under neutral conditions for about 1 to 6 hours, with other suitable reaction media including acetic acid or concentrated hydrochloric acid, and other suitable metals including zinc.

4-Acetamido-3-nitrobenzoic acid is converted to the corresponding benzoyl chloride, as exemplified by step (3) above, by treatment with thionyl chloride with or without an inert diluent (e.g., benzene, methylene chloride, chloroform, etc.) at about 20°–80° C.

Conversion of an acylamino group, for example, an acetamido group, to an amino group, as exemplified by step (5) above, can be effected by treating the acylamino group-containing compound with a strong acid, such as hydrochloric acid, or strong base, such as sodium hydroxide, potassium hydroxide, potassium carbonate, or sodium carbonate in aqueous methanol at about 20° C. to about 100° C. for about ¼ hour to about 24 hours. The 1-amino-2-nitro-5-heterocyclic-carbonylbenzene resulting from step (5) can also be prepared by treating the corresponding 5-carboxy compound to form the acid anhydride or acid halide thereof, and then reacting the latter compound with a heterocyclic base, for example as set forth above with regard to steps (1) and (4).

Conversion of a hetero sulfur atom in the heterocyclic ring

to the sulfoxide or sulfone form, or conversion of a hetero sulfur atom already in the sulfoxide form to the sulfone form, is conveniently effected by treatment with hydrogen peroxide in glacial acetic acid, nitric acid or chromic acid with glacial acetic acid or a peracid, such as peracetic acid, perbenzoic acid, metachloroperbenzoic acid, perphthalic acid, or pertrifluoroacetic acid in an inert solvent for the compound being treated. Suitable solvent materials include, for example, methylene chloride or chloroform. If the compound being treated is not soluble in the particular reaction media desired to be utilized, then a co-solvent material, such as acetic acid or methanol, should be utilized in an amount sufficient to dissolve the compound being treated. Typically, the reaction is conducted at a temperature from about −30° C. to about room temperature for about ½ hour to about 6 hours. When it is desired to convert the hetero sulfur atom to the sulfoxide form, molar quantities are utilized, and reaction conditions are carefully monitored to insure that the reaction does not proceed further than desired. When it is desired to convert the hetero sulfur atom to the sulfone form, or it is desired to convert the sulfoxide to the sulfone, an excess of the oxidizing material, for example, 2 moles of a peracid per mole of the compound being treated, is utilized and the reaction conditions do not have to be as carefully monitored. Optionally, such conversions can also be effected by treatment with periodate in aqueous methanol or aqueous acetonitrile at a temperature in the range of about −20° C. to about 50° C. for about ½ to about 12 hours.

In each of the process steps, described herein above and below, unless otherwise indicated, the respective intermediate products are not separated from the reaction mixtures. If desired, however, they can be separated and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the scope of the present invention but not particularly described in this specification, will be apparent to those skilled in this art.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION 1

175 G. of S-methyl isothiouronium sulfate in one liter of water is cooled to 0° C. and 162.5 g. of methylchloroformate added, followed by the addition of a solution of 250 g. potassium hydroxide in 750 ml. water at 0° to 5° C. The crude product is extracted into benzene, the benzene dried and evaporated, and the residue recrystallized from methanol. 1,3-Bis(methoxycarbonyl)-S-methyl isothiourea is thus obtained.

In a similar manner, substituting ethylchloroformate, propylchloroformate and butylchloroformate for the methylchloroformate, 1,3-bis(ethoxycarbonyl)-S-methyl isothiourea, 1,3-bis(propoxycarbonyl)-S-methyl isothiourea, and 1,3-bis(butoxycarbonyl)-S-methyl isothiourea are, respectively, prepared.

PREPARATION 2

7.6 G (0.1 mol) of thiourea and 10 ml of water are mixed inside a 4-neck flask of 200 ml capacity equipped with an agitator, condenser, pipet and a thermometer and the mixture is agitated. 10.4 G. (0.11 mol) of methyl chloroformate is added dropwise using the pipet at room temperature and the mixture is left standing for about 20 minutes until the crystals of thiourea are completely dissolved. The mixture is heated then left standing for 30 minutes at temperatures in the range of 90°~100° C. It is cooled with ice water and 12.3 g (0.13 mol) of methyl chloroformate is added while the temperature is maintained at 5° C. Thereafter about 45 g of a 25%-water solution of caustic soda is gradually added dropwise through the pipet to adjust the pH value to approximately 7. This requires about 30 minutes. The temperature was further maintained in the range of 10°~15° C. for 2 hours. The crude product is extracted into benzene, the benzene dried and evaporated, and the residue is recrystallized from methanol to give what is believed to be 1,3-bis(methoxycarbonyl)-S-methyl isothiourea.

In a similar manner, substituting ethylchloroformate, propylchloroformate and butylchloroformate for the methylchloroformate, 1,3-bis(ethoxycarbonyl)-S-methyl isothiourea, 1,3-bis(propoxycarbonyl)-S-methyl isothiourea, and 1,3-bis(butoxycarbonyl)-S-methyl isothiourea are, respectively, prepared. The resulting reagents are then reacted with suitable phenylenediamines as set forth in the Examples hereafter.

EXAMPLES I–XII

A solution of 17.4 g. (0.075 mol.) of 3,4 dinitrobenzoylchloride in 250 ml of methylene chloride is treated at 0°–20° C. with a solution of 13 g. (0.15 mol.) of morpholine in 100 ml. of methylene chloride. The solution is kept at 20°–25° C. for 2 hrs., the solvent is evaporated and the residue triturated with water. Recrystallization from methanol affords 4-morpholinocarbonyl-1,2-dinitrobenzene (m.p. 136°–137° C.). 17.0 G. of 4-morpholinocarbonyl-1,2-dinitrobenzene in 340 ml. of methanol is hydrogenated for 3 hrs. at 45–50 psi in the presence of 1.7 g. of 5% palladized charcoal. The resulting solution of 1,2-diamino-4-morpholinocarbonylbenzene is filtered and concentrated to ~170 ml. 14.0 G. of 1,3-bis-methoxycarbonyl-S-methyl isothiourea, 170 ml. of water and 4 ml. of acetic acid are added to the diamine solution and the mixture is refluxed for 3 hrs. The solution is concentrated and cooled. Filtration and recrystallization from methanol-chloroform affords 5(6)-morpholinocarbonyl-2-carbomethoxyaminobenzimidazole (m.p. 224° C. dec.).

In similar manner, substituting:
4-methylpiperazine;
piperidine;
thiomorpholine;
pyrrolidine;
thiazolidine;
2,6-dimethylpiperidine;
2,6-dimethylmorpholine;
4-hydroxypiperidine;
2-methylpiperidine;
3-methylpiperidine; or
4-methylpiperidine;
for the morpholine, the following compounds are prepared:

5(6)-(4-methylpiperazinylcarbonyl)-2-carbomethoxyaminobenzimidazole (m.p. 217°–220° C. dec.);

5(6)-piperidinocarbonyl-2-carbomethoxyaminobenzimidazole (m.p. 203°–207° C. dec.);

5(6)-thiomorpholinocarbonyl-2-carbomethoxyaminobenzimidazole (m.p. 242°–243° C. dec.);

5(6)-pyrrolidinylcarbonyl-2-carbomethoxyaminobenzimidazole (m.p. 221°–222° C. dec.);

5(6)-thiazolidin-3-ylcarbonyl-2-carbomethoxyaminobenzimidazole (m.p. 244° C. dec.);

5(6)-(2-6-dimethylpiperidinocarbonyl)-2-carbomethoxyaminobenzimidazole (m.p. 206°–214° C.);

5(6)-(2,6-dimethylmorpholinocarbonyl)-2-carbomethoxyaminobenzimidazole (m.p. ~245° C. dec.);

5(6)-(4-hydroxypiperidinocarbonyl)-2-carbomethoxyaminobenzimidazole (m.p. ~270° C. dec.);

5(6)-(2-methylpiperidinocarbonyl)-2-carbomethoxyaminobenzimidazole;

5(6)-(3-methylpiperidinocarbonyl)-2-carbomethoxyaminobenzimidazole; and

5(6)-(4-methylpiperidinocarbonyl)-2-carbomethoxyaminobenzimidazole; respectively.

In a similar manner, substituting 1,3-bis(ethoxycarbonyl)-S-methyl isothiourea, 1,3-bis(propoxycarbonyl)-S-methyl isothiourea, 1,3-bis(butoxycarbonyl)-S-methyl isothiourea for the 1,3-bis(methoxycarbonyl)-S-methyl isothiourea, the corresponding compounds are prepared where R is ethyl, propyl or butyl, including, for example, 5(6)-morpholinocarbonyl-2-carbethoxyaminobenzimidazole, 5(6)-morpholinocarbonyl-2-carbopropoxyaminobenzimidazole, and 5(6)-morpholinocarbonyl-2-carbobutoxyaminobenzimidazole.

EXAMPLE XIII 1.52 G. of 5(6)-morpholinocarbonyl-2-carbomethoxyaminobenzimidazole is dissolved in a mixture of 2 ml. of water and 0.5 ml. of concentrated hydrochloric acid, and the resulting solution is diluted with 100 ml. of acetone. After 6 hrs. at ~20° C., the product is filtered off to afford the hydrochloride salt of 5(6)-morpholinocarbonyl-2-carbomethoxyaminobenzimidazole (m.p. 180°–182° C. dec.).

EXAMPLE XIV

5 G. of 3,4 dinitrobenzoic acid is hydrogenated in 100 ml. of methanol in the presence of 1 g. of 5% palladized charcoal at 40–50 psi. The catalyst is filtered off and the filtrate concentrated to ~40 ml. To this solution there is added 5 g. of 1,3 bismethoxycarbonyl-S-methyl isothiourea, 40 ml. of water and 2 ml. of acetic acid. The mixture is refluxed for 3 hrs., cooled, filtered and washed well with water and methanol to afford 5(6)-carboxy-2-carbomethoxyaminobenzimidazole (m.p. >310° C.).

0.6 G. of 5(6)-carboxy-2-carbomethoxyaminobenzimidazole is suspended in 30 ml of tetrahydrofuran and 1 ml. of trifluoroaceticanhydride is added. The mixture is stirred at 20°–25° C. for ~6–10 hrs. until homogeneous. Then 2 ml. of 1,2,3,6 tetrahydropyridine is added with cooling at 15°–20° C. The mixture is stirred for 3 hrs. at 20°–25° C., concentrated under vacuum and the residue diluted with water and extracted with chloroform. The chloroform extracts are washed with water, dried (MgSO$_4$) and evaporated. The residue is recrystallized for methanol to afford 5(6)-(1,2,3,6-tetrahydropyridyl)-2-carbomethoxyaminobenzimidazole (m.p. ~243° C. dec.).

EXAMPLES XV–XVI 0.64 G. of 5(6)-thiomorpholinocarbonyl-2-carbomethoxyaminobenzimidazole is dissolved in a mixture of 3 ml. of acetic acid and 30 ml. of chloroform. A solution of 0.42 g. of meta-chloroperbenzoic acid in 20 ml. of chloroform is added at −15° to −10° C., then the mixture is allowed to warm slowly to ~20°–25° C. After ~6 hours, the solvent is removed under vacuum at 20°–30° C. and the residue treated with sodium bicarbonate solution. The product is filtered off and recrystallized from methanol-chloroform to afford 5(6)-(1-oxo-thiomorpholinocarbonyl)-2-carbomethoxyaminobenzimidazole (m.p. 249°–250.5° C. dec.).

In a similar manner, substituting thiazolidine for the thiamorpholine, there is prepared 5(6)-(1-oxo-thiazolidin-3-ylcarbonyl)-2-carbomethoxyaminobenzimidazole (m.p. ~270° C. dec.).

In similar manner to the last paragraph of Example I, compounds corresponding to the compounds of these Examples XV and XVI are prepared where R is ethyl, propyl and butyl.

EXAMPLES XVII–XVIII

In similar manner to the first two paragraphs of Examples XV and XVI above, using an extra equivalent of metachloroperbenzoic acid, 5(6)-(1,1-dioxo-thiomorpholinocarbonyl)-2-carbomethoxyaminobenzimidazole and 5(6)-(1,1-dioxothiazolidin-3-ylcarbonyl)-2-carbomethoxyaminobenzimidazole are prepared, respectively.

In similar manner to the last paragraph of Example I, compounds corresponding to the compounds of these Examples XVII and XVIII are prepared where R is ethyl, propyl, and butyl.

EXAMPLE XIX

Four young Swiss-Webster male mice (16–20 g.) are artificially infected with 200 larvae of the species Nematospiroides dubius (roundworm) and Hymenolepis nana (tapeworm) and naturally infected with 15–40 larvae of Syphacia obvelata and Aspiculuris tetraptera (pinworms). The drug is administered in a commercial rat/mouse diet at the stated dose(s) from day 1 through day 18, the infection being introduced at day 0. The animals are sacrificed at day 18 and the parasites remaining in the entire small intestine, cecum and large bowel are counted and differentiated. The average number of each parasite remaining in each medicated group is compared to the average number remaining in the control. This comparison is expressed as percent reduction over the parasites in the control group. The data for illustrative compounds of this invention is tabulated in the Table below.

5(6)-Z⟩N—C(=O)-2-carbomethoxyaminobenzimidazoles

| Z⟩N— | dose,* ppm | Test species (% reduction) | | | |
|---|---|---|---|---|---|
| | | Nd | Hn | So | At |
| morpholino | 125 | 100 | 78 | 100 | 100 |
| | 62.5 | 100 | 0 | 100 | 100 |
| | 31 (2) | 100 | 0 | 100 | 70 |
| | 16 | 87 | 0 | 100 | 37 |
| | 8 | 0 | 0 | 100 | 0 |
| piperidino | 125 | 66 | 29 | 100 | 100 |
| | 62 | 0 | 0 | 100 | 100 |
| thiamorpholino | 125 | 69 | 0 | 100 | 100 |
| | 62 | 0 | 0 | 100 | 100 |
| pyrrolidinyl | 125 | 100 | 0 | 100 | 100 |
| | 62 | 64 | 0 | 100 | 100 |
| thiazolidin-3-yl | 125 | 59 | 0 | 100 | 100 |
| | 62 | 0 | 0 | 100 | 100 |
| 1,2,3,6-tetrahydropyridyl | 62 | 84 | 0 | 100 | 100 |
| | 31 | 0 | 0 | 100 | 100 |
| 1-oxo-thiomorpholino | 62 | 0 | 0 | 100 | 100 |
| | 31 | 0 | 0 | 100 | 100 |
| 1-oxo-thiazolidin-3-yl | 62 | 0 | 0 | 100 | 100 |

Nd = Nematospiroides dubius
Hn = Hymenolepis nana
So = Syphacia obvelata
At = Aspiculuris tetraptera
*The number in parentheses refers to the number of runs from which percent reductions are calculated and averaged to give the data set forth for that particular dose in this Table.

EXAMPLE XX

A formulation is prepared having the following composition:
  5(6)-morpholinocarbonyl-2-carbomethoxyaminobenzimidazole: 30%
  polyethylene glycol 6000: 40%

Myrj 52 [polyoxy(40) stearate; a product of Altas Chemical Co.]: 30%

This formulation is prepared by heating the polyethylene glycol 6000 and Myrj 52 to 55°–60° C. and, when completely melted, the 5(6)-morpholinocarbonyl-2-carbomethoxyaminobenzimidazole is added with stirring until homogeneous. The formulation is solidified by cooling and ground, without remelting of the polyethylene glycol, to a fine powder.

EXAMPLE XXI

A drench powder is prepared having the following composition:
The formulation of Example XX: 15.1 g.
Cabosil M-5 (colloidal silica; Cabot corp.): 6.0 g.
Carboxymethyl cellulose (7M8-SXF): 6.0 g.

The comelt formulation and carboxymethyl cellulose are blended together until uniform, then the Cabosil is added, the mixture blended until once again uniform, and then finely powdered.

EXAMPLE XXII

A suspension is prepared having the following formulation:
The formulation of Example XX: 7.550 g.
Citric acid, hydrous: 0.431 g.
sodium citrate: 0.868 g.
carboxymethyl cellulose (7M8-SXF): 1.051 g.
Cabosil M-5: 1.000 g.
sorbic acid: 0.300 g.
purified water: to 100.00 ml.

The sorbic acid, citric acid and sodium citrate are added to 90 ml. of water which has been heated to 80° C. The Cabosil and carboxymethyl cellulose are then added, with stirring, until uniformly dispersed and fully hydrated. The mixture is cooled to 45° C., and the formulation of Example XX is added, with stirring, until it is uniformly dispersed. The suspension is cooled to room temperature and the balance of the water is added.

EXAMPLE XXIII

A top dressing for horses is prepared having the following composition:

| | |
|---|---|
| The formulation of Example XX | 8.550 g. |
| granular sucrose | 17.450 g. |
| | 25.000 g. |
| water | 1.00 ml. |

EXAMPLE XXIV

A top dressing for cattle is prepared having the following composition:
The formulation of Example XX: 75.52 g.
Soybean meal: 2196.30 g.

If desired, the soybean meal can be replaced with alfalfa meal or corn gluten meal.

EXAMPLE XXV

A cattle feed additive is prepared having the following composition:

| | |
|---|---|
| The formulation of Example XX | 22.24 g. |
| feed excipient (Soybean meal, or corn gluten meal | 77.76 g. |
| | 100.00 g. |

EXAMPLE XXVI

A cattle bolus is prepared having the following composition:
The formulation of Example XX: 1.89 g.
Starch: 0.5–2.0 g.
Talc: 0.05–2.0 g.
Magnesium stearate: 0.05–2.0 g.
sodium chloride: 0.5–5.0 g.
lactose: 3.0–8.0 g.

EXAMPLE XXVII

A cattle paste is prepared having the following composition:
The formulation of Example XX: 6%
Corn oil: 85–90%
Antioxidant (e.g., a mixture of butylated hydroxy anisole and butylated hydroxy toluene): 0.1–0.5%
Benzoic acid: 0.3%
Thickener (e.g., Cabosil M-5): 6–10%

EXAMPLE XXVIII

An equine paste is prepared having the following composition:

| | |
|---|---|
| The formulation of Example XX | 48% |
| Vegetable oil (e.g., corn oil) | 40–60% |
| Other fatty acid glycerides | 10–20% |
| Antioxidant (e.g., a mixture of butylated hydroxy anisole and butylated hydroxy toluene) | 0.1–0.5% |
| Benzoic acid | 0.3% |
| Thickener (e.g., Cabosil M-5) | 1–5% |
| | 100% |

EXAMPLE XXIX

An oral suspension for human use is prepared having the following composition:

| | |
|---|---|
| 5(6)-morpholinocarbonyl-2-carbomethoxyaminobenzimidazole | 2.5% |
| Benzoic acid | 0.3% |
| Veegum K | 3.0% |
| Citric acid | 0.4% |
| Sodium citrate | 0.8% |
| Sodium saccharin | 0.01% |
| Mangasweet 100 | 0.02% |
| Flavor | 0.03% |
| Color | 0.0025% |
| Water Q.S. | to 100% |

Benzoic acid, citric acid and saccharin citrate are dissolved in 90 ml of water which has been heated to 95°–100° C. Veegum K is added slowly and allowed to fully hydrate. The resultant suspension is cooled to room temperature and Magnasweet 100 and saccharin are added. The active drug is stirred in, color and flavor are added and the additional water added as necessary. The suspension is milled through a colloid mill to assure uniform dispension.

EXAMPLE XXX

A tablet for human use is prepared having the following composition:

| | | |
|---|---|---|
| 5(6)-morpholinocarbonyl-2-carbomethoxyaminobenzimidazole | 40% | 100 mg |
| Starch | 15% | 37.5 mg |
| Mangesium stearate | 1% | 2.5 mg |
| Talc | 2% | 5.0 mg |
| Color (lake) | 0.24% | 0.6 mg |
| Lactose | 41.76% | 104.4 mg |
| | | 250.4 mg |
| Water | | .08 ml |

Half of the lactose is blended with the color lake, then the balance of lactose is added and blended. The active drug is added to the lactose blend and mixed until uniform. The starch past is prepared, granulated, screened and dried to the desired moisture content. The dried granulation is screened, lubricants are added and mixed. Tablets are then prepared on a suitable tablet press.

EXAMPLE XXXI

A solution of 2.31 g of 3,4-dinitrobenzoylchloride in 50 ml of methylene chloride is heated at 20°–25° C. with 1.3 g of 3-pyrroline. After 1 to 2 hours the solution is washed with 5% hydrochloric acid, water and dried over magnesium sulfate. The solvent is evaporated and residual 1,2-dinitro-4-(3-pyrrolinylcarbonyl)benzene recrystallized from methanol.

1.2 G. of the above-described dinitrocompound is dissolved in 10 ml of methanol and 10 ml of water containing 1.2 g of iron powder and 0.25 ml of conc. hydrochloric acid. The mixture is refluxed until reduction is complete (~4 hours), charcoal is added and the solution filtered. 1 G. of 1,3-bis-methoxycarbonyl-2-methylisothiourea and 0.3 ml acetic acid are added and the solution refluxed for 4–5 hours. The cooled reaction mixture is filtered and the crude product recrystallized from methanol-chloroform to afford 5(6)-(3-pyrrolinylcarbonyl)-2-carbomethoxyaminobenzimidazole.

EXAMPLES XXXII–XXXIII

In a similar manner to the procedure to Example I, substituting perhydroazepine and perhydroazocine for morpholine, 5(6)-(perhydroazepinylcarbonyl)-2-carbomethoxyaminobenzimidazole (m.p. 221°–5° C.) and 5(6)-(perhydroazocinylcarbonyl)-2-carbomethoxyaminobenzimidazole, and the corresponding compounds where R is ethyl, propyl or butyl, are prepared.

EXAMPLES XXXIV–XXXV

Also in similar manner to the procedure of Example I, substituting 4-phenylpiperazine and 4-benzylpiperazine for the morpholine, there are prepared 5(6)-(4-phenylpiperazinylcarbonyl)-2-carbomethoxyaminobenzimidazole and 5(6)-(4-benzylpiperazinylcarbonyl)-2-carbomethoxyaminobenzimidazole. In this Example XXXV, the iron reduction technique of Example XXXI is utilized in place of the catalytic hydrogenation of Example I.

EXAMPLES XXXVI–XXXVIII 1.24 G. of 5(6)-(morpholinocarbonyl)-2-carbomethoxyaminobenzimidazole is suspended in 25 ml of tetrahydropyran. 1 Ml of n-butylisocyanate is added and the mixture stirred overnight (~15 hours). The solution is evaporated to dryness under vacuum and the residue triturated with methanol to afford 1-(n-butylcarbamoyl)-5(6)-(morpholinocarbonyl)-2-carbomethoxyaminobenzimidazole (m.p. 220°–2° C.).

In similar manner to the above, substituting methylisocyanate and phenylisocyanate for the n-butylisocyanate, and triturated with acetone in place of methanol, 1-methylcarbamoyl-5(6)-(morpholinocarbonyl)-2-carbomethoxyaminobenzimidazole and 1-phenylcarbamoyl-5(6)-(morpholinocarbonyl)-2-carbomethoxyaminobenzimidazole are prepared, respectively.

EXAMPLE XXXIX 11.2 G. of 3-nitro-4-acetamidobenzoic acid [prepared as described in Helv. Chem. Acta 36, 806 (1953)] is suspended in 50 ml of methylene chloride and treated with 5 ml of thionyl chloride and 5 drops of dimethylformamide. The mixture is refluxed until the reaction is complete (~3 hours). The solution is cooled and treated at 10°–20° C. with 18 ml of morpholine and left overnight. 25 Ml of water and 10 ml of conc. hydrochloric acid are added. The lower layer is separated and washed with water, and a 5 ml wash of methylene chloride is combined with the main solution. 50 Ml of methanol and 10 ml of 5 N sodium hydroxide solution is added at 20°–25° C. After 1 hour, the mixture is neutralized with ~1 ml of acetic acid and concentrated under vacuum to a volume of ~50–60 ml. Water is added until the total volume is about ~200 ml and 2-nitro-4-morpholinocarbonylaniline filtered off and dried.

The preparation of 2-acetamido-5-morpholinocarbonylaniline, an unisolated intermediate in the above procedure, is also described in Chem. Absts. 58:45416 (1963).

2.5 G. of 2-nitro-4-morpholinocarbonylaniline, 2.5 g of iron powder, 10 ml of methanol, 10 ml of water and 0.5 ml of conc. hydrochloric acid are heated under nitrogen at reflux until reduction is complete (~30 minutes). The mixture is cooled and filtered through charcoal. 2.1 G of 1,3-bismethoxycarbonyl-S-methyl isothiourea and 0.6 ml of acetic acid are added and the mixture heated for 3 hours at reflux. The pH is adjusted to 7 with ammonium hydroxide and the methanol distilled off under vacuum. The solution is cooled, the product filtered off after a suitable aging period, recrystallized from methanol-chloroform with charcoal treatment to afford 5(6)-morpholinocarbonyl-2-carbomethoxyaminobenzimidazole.

EXAMPLE XXXX

A solution of 0.14 g of ferrous sulfate heptahydrate in 15 ml of methanol is treated under nitrogen with 0.02 g of sodium borohydride. After 5 minutes, 2.5 g of 2-nitro-4-morpholinocarbonylaniline (as prepared in Example XXXIX) and 1 ml 64% hydrazine are added. The mixture is refluxed until reduction is complete (~4–6 hours) to afford 1,2-diamino-4-morpholinocarbonylbenzene.

4 G. of calcium cyanamide is suspended in 15 ml of water and 3.7 ml of ethanol. 2.7 Ml of methylchloroformate is added dropwise at 30°–40° C. After 1 hour more at 30°–40° C. the mixture is filtered.

The mixture is of 1,2-diamino-4-morpholinocarbonylbenzene is cooled, filtered and treated with 25 ml of the reagent prepared in the preceeding paragraph, and the pH adjusted to 3 by addition of hydrochloric acid. The mixture is heated and kept at pH 3–4 (by addition of additional hydrochloric acid as necessary) for 3 hours, cooled and pH adjusted to 7.0 with ammonia hydroxide. After 24 hours, 5(6)-morpholinocarbonyl-2-carbomethoxyaminobenzimidazole is filtered off.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A compound selected from the group of compounds represented by the formula:

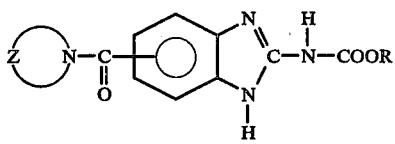

where R is a lower alkyl group having 1 to 4 carbon atoms;

is a saturated 6 membered heterocyclic ring containing only 1 nitrogen and 1 oxygen as the only hetero atoms and which is optionally substituted with 1 hydroxy, phenyl, benzyl or oxo radical or 1 or 2 alkyl groups; the

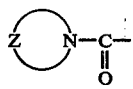

substitution being at the 5(6)- position; or a pharmaceutically acceptable salt thereof.

2. The compound of claim 1 wherein R is methyl.

3. The compound of claim 1 wherein said heterocyclic ring, expressed in radical form, is selected from the group consisting of: morpholino and 2,6-dimethylmorpholino.

4. The compound of claim 1 wherein said heterocyclic ring is morpholino.

5. The compound of claim 1 wherein said compound of Formula I is 5(6)-morpholinocarbonyl-2-carbomethoxyaminobenzimidazole.

6. A composition for controlling helminths in mammals comprising a pharmaceutically acceptable nontoxic excipient and an anthelmintically effective amount of a compound selected from the group of compounds represented by the formula:

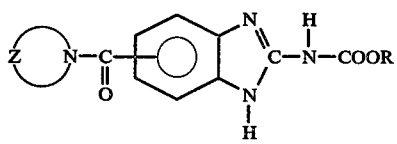

where R is a lower alkyl group of 1 to 4 carbon atoms;

is a saturated 6 member heterocyclic ring containing only one nitrogen and one oxygen as the only hetero atoms and which is optionally substituted with 1 hydroxy, phenyl, benzyl or oxo radical or 1 or 2 alkyl groups; the

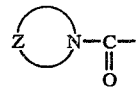

substitution being at the 5(6)-position; or a pharmaceutically acceptable salt thereof.

7. The composition of claim 6 wherein R is methyl.

8. The composition of claim 6 wherein said heterocyclic ring, expressed in radical form, is selected from the group consisting of: morpholino and 2,6-dimethylmorpholino.

9. The composition of claim 6 wherein said heterocyclic ring is morpholino.

10. The composition of claim 6 wherein said compound of Formula I is 5(6)-morpholinocarbonyl-2-carbomethoxyaminobenzimidazole.

11. The composition of claim 6 wherein said excipient is water and said compound is selected from the pharmaceutically acceptable salts of said group of compounds represented by formula I.

12. The composition of claim 11 wherein said compound is a pharmaceutically acceptable salt of 5(6)-morpholinocarbonyl-2-carbomethoxyaminobenzimidazole.

13. A method for controlling helminths in mammals which comprises administering an anthelmintically effective amount of a compound selected from the group of compounds represented by the formula:

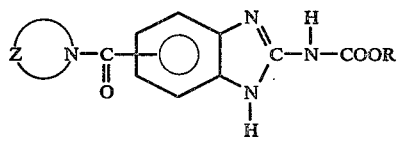

where R is lower alkyl group having 1 4 carbon atoms;

is a saturated 6 membered heterocyclic ring containing only one nitrogen atom and one oxygen atom as the only hetero atoms and which is optionally substituted with 1 hydroxy, phenyl, benzyl or oxo radical or 1 or 2 alkyl groups; the

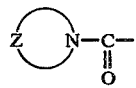

substitution being at the 5(6)-position; or pharmaceutically acceptable salt thereof.

14. The method of claim 13 wherein R is methyl.

15. The method of of claim 13 wherein said heterocyclic ring, expressed in radical form, is selected from the group consisting of: morpholino and 2,6-dimethylmorpholino.

16. The method of claim 13 wherein said compound of Formula I is 5(6)-morpholinocarbonyl-2-carbomethoxyaminobenzimidazole.